United States Patent [19]

Thompson et al.

[11] Patent Number: 5,002,536
[45] Date of Patent: Mar. 26, 1991

[54] GUARDED NEEDLE COVER

[76] Inventors: John P. Thompson; Ivy L. Thompson, both of 2327 Eagle Park, Arlington, Tex. 76011

[21] Appl. No.: 106,421

[22] Filed: Oct. 9, 1987

Related U.S. Application Data

[63] Continuation-in-part of Ser. No. 85,809, Aug. 17, 1987, abandoned.

[51] Int. Cl.$^5$ .............................................. A61M 5/32
[52] U.S. Cl. .................................. 604/192; 604/272; 128/763
[58] Field of Search ............... 128/763, 764, 766, 770; 604/51, 52, 201, 204, 272, 411–415

[56] References Cited

U.S. PATENT DOCUMENTS

| | | | |
|---|---|---|---|
| 4,312,362 | 1/1982 | Kaufman | 128/763 |
| 4,326,540 | 4/1982 | Baiky et al. | 128/763 |
| 4,340,067 | 7/1982 | Rattenborg | 128/763 |
| 4,372,325 | 2/1983 | Raitto | 128/763 |
| 4,623,336 | 11/1986 | Pedicano | 604/110 |
| 4,673,399 | 6/1987 | Pruett | 604/86 |

FOREIGN PATENT DOCUMENTS 1491784  5/1964  Fed. Rep. of Germany ...... 604/201

Primary Examiner—Max Hindenburg
Attorney, Agent, or Firm—Crutsinger & Booth

[57] ABSTRACT

A hypodermic syringe including a connector member for securing the proximal end of a hollow needle to the distal end of the syringe and a hollow protective elastomeric sleeve having a closed end and an open end, the open end having an inside diameter which is less than the outside diameter of the connector member. A shoulder is formed about the exterior of the open end of the protective sleeve forming a resilient deformable end section on the sleeve which is deformable to grippingly engage the outside of the connector member. An enlarged hollow truncated conical shaped guide member is secured to the sleeve to guide the sharp pointed hollow needle into the open end of said elastomeric sleeve to shield the hand of a health care worker against needle stick injuries. Locking lugs on the inner wall of the protective sleeve between opposite ends thereof detachably engage a non-circular end of the connector member when the conical shaped end of the connector member is urged into deforming frictional engagement with the inner wall of said sleeve.

8 Claims, 2 Drawing Sheets

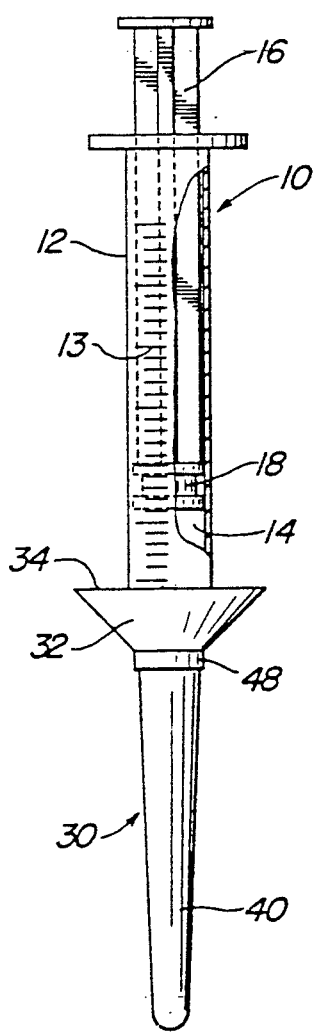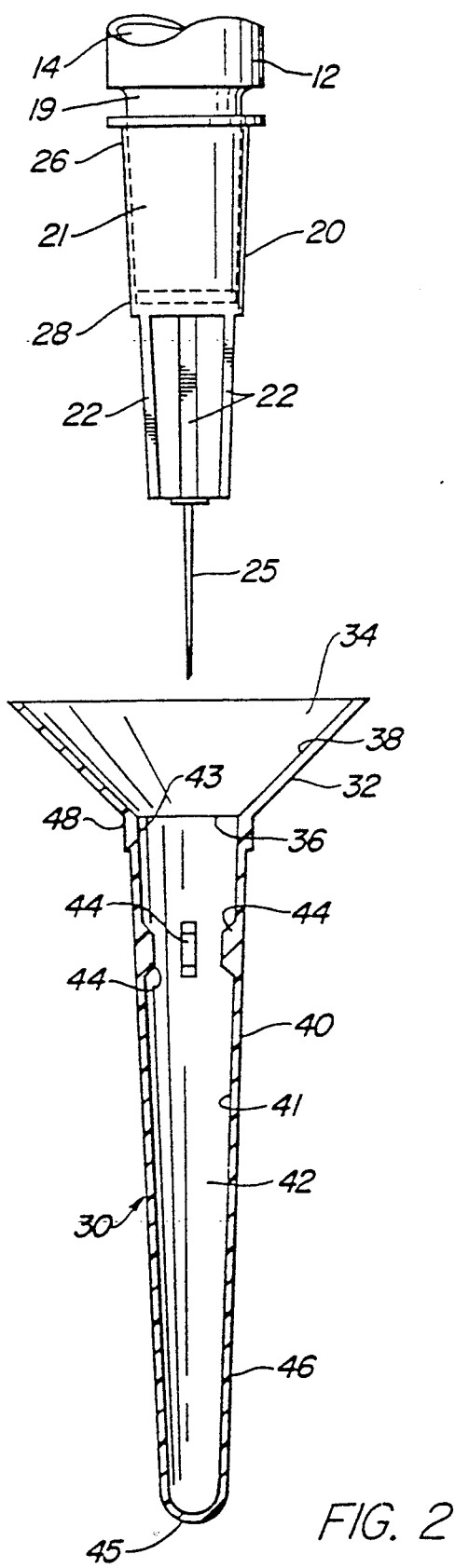
FIG. 1
FIG. 2

GUARDED NEEDLE COVER

CROSS-REFERENCE TO RELATED APPLICATIONS

This application is a continuation-in-part of our co-pending application Ser. No. 085,809 filed Aug. 17, 1987, entitled "VACUUM BLOOD COLLECTION SYSTEM", now abandoned.

TECHNICAL FIELD

A hypodermic syringe for injecting liquid into a body or for withdrawing body fluids which includes a funnel shaped guide surface on a protective sleeve to facilitate insertion of a needle into the protective sleeve after use and to shield the hand of a health care worker from needlesticks.

BACKGROUND OF INVENTION

Health care workers are caring for increasing numbers of AIDS patients. Several studies are underway investigating occupational risks of acquired immunodeficiency syndrome (AIDS) among health workers.

Needlestick injuries and cuts with sharp instruments according to one survey accounted for 76% of the exposures of health care workers to blood or other body fluids of patients with acquired immunodeficiency syndrome (AIDS) or AIDS-related illnesses.

While extensive educational programs have been initiated to train medical personnel in proper techniques for working with AIDS patients, the risk of becoming infected with the incurable AIDS virus has resulted in some health workers refusing to care for AIDS patients.

U.S. Pat. No. 4,623,336 discloses a disposable safety needle sheath having a funnel-shaped receiving end to protect the user's hand and guide a used needle into a sleeve. The sheath is provided with a cap hingedly connected to the funnel-shaped receiving guide and a locking mechanism to prevent the sheath from being reopened after a used needle has been inserted and the cap closed. A second embodiment includes a kit comprising a syringe, needle and the disposable safety needle sheath sealed in a tamper-proof package. The tamper-proof package is opened to access the sterile needle for use. The patent teaches that the used needle should be reinserted into the sheath, disconnected from the syringe, and sealed in the sheath by closing the locking cap. The flange on the funnel-shaped needle sheath is described as being up to three inches in diameter to provide a shield for protecting the hand and fingers of a user while guiding the sharp needle into a reduced diameter shaped opening in the sheath.

The apparatus described in the aforementioned patent is apparently intended for use primarily as an auxiliary disposable package into which a used needle is inserted for disposal. Many busy health care workers faced with life or death decisions will not search for an auxiliary device. Further, auxiliary devices tend to be at a different location when needed.

Educational programs for health care workers recommended by the American Hospital Association and the Centers for Disease Control differ from traditional infection prevention programs in that it provides the same level of precautions for all patients, rather than singling out those with diagnosed infections. Thus, a need exists for a guarded needle cover to protect health care workers against needle stick injuries which will be used routinely during treatment of all patients as opposed to an auxiliary device which is used only during treatment of patients with diagnosed infections.

SUMMARY OF INVENTION

The improved syringe and guarded needle cap hereinafter described and illustrated in the attached drawing is devised to alleviate problems heretofore encountered. The hypodermic syringe to inject liquid into a body or to withdraw body fluids includes a hollow needle having a sharp pointed distal end and a proximal end; a connector member for securing the proximal end of the hollow needle to the distal end of the container; and a protective sleeve.

The improved hollow protective elastomeric sleeve has a closed end and an open end, the open end having an inside diameter which is less than the outside diameter of a connector member used to mount the needle on a syringe. A shoulder about the exterior of the open end of the protective sleeve forms a resilient deformable end section on the sleeve to grippingly engage the outside diameter of the connector member.

An enlarged hollow truncated conical shaped guide member secured to the shoulder, and has an enlarged proximal end and a reduced diameter distal end bounded by an inclined guide surface configured to guide the sharp pointed hollow needle into the open end of the elastomeric sleeve. Locking apparatus on the inner wall of the protective sleeve between opposite ends thereof detachably engage the end of the connector member when the conical shaped end of the connector member is urged into deforming frictional engagement with the inner wall of the sleeve adjacent the shoulder.

It is very important that the protective sleeve be used as nearly as possible in the same manner and according to the same procedure with which health care workers are accustomed.

DESCRIPTION OF THE DRAWINGS

Drawings of two embodiments of the invention are annexed hereto so that the invention may be better and more fully understood, in which:

FIG. 1 is an elevational view of a hypodermic syringe with a protective sleeve secured thereto;

FIG. 2 is an enlarged exploded elevational view of a protective sleeve and syringe connector member, parts being broken away to more clearly illustrate details of construction;

Numeral references are employed to designate like parts throughout the various figures of the drawing.

DESCRIPTION OF PREFERRED EMBODIMENTS

Figure 3:
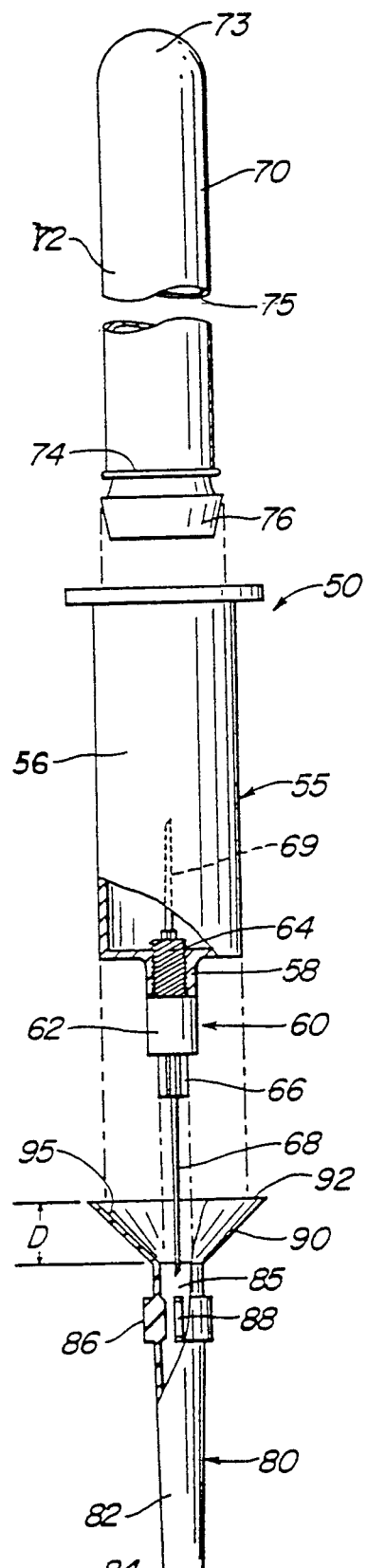
FIG. 3 is an enlarged exploded elevational view of a blood collection system with a protective sleeve attached thereto.
Figure 4:
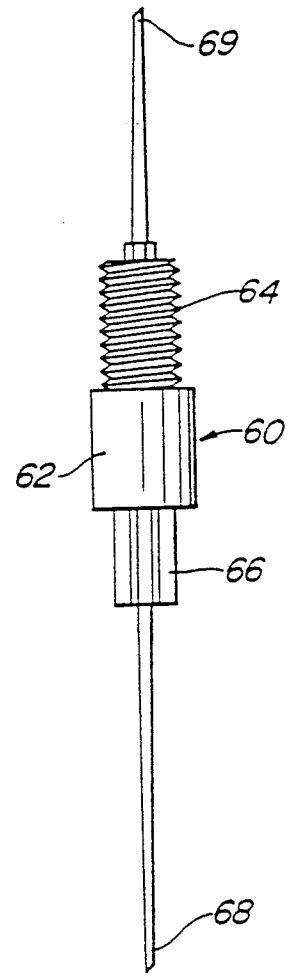
FIG. 4 is an elevational view of a cannula connector member disconnected from the cannula tube of a blood collection system.

Two embodiments of apparatus for injecting and withdrawing fluids incorporating a protective needle cover are illustrated in the drawings. A first embodiment comprising a hypodermic syringe is illustrated in FIGS. 1 and 2 of the drawing. A second embodiment comprising a blood collection system is illustrated in FIGS. 3 and 4 of the drawing.

FIRST EMBODIMENT

Referring to FIGS. 1 and 2 of the drawing, the numeral 10 generally designates a hypodermic syringe which is of conventional design and is commercially available from Becton, Dickinson & Co. of Rutherford, N.J. Hypodermic syringe 10 comprises a hollow barrel 12 having a bore 14 formed therein through which a plunger 16 having a piston 18 on the end thereof is slidably disposed. Piston 18 has sealing elements on the outer periphery thereof which sealingly engage the inner wall of bore 14 for changing pressure inside bore 14 for drawing liquid into the bore or for dispensing liquid therefrom. Indicia 13 printed on barrel 12 indicate the volume of liquid in bore 14.

As best illustrated in FIG. 2 of the drawing, the distal end of hollow barrel 12 has a projection 19 formed on the end thereof which extends into a hollow bore in needle connector 20. Needle connector 20 has a body portion 21 having a major diameter at one end 26 and a smaller diameter at the other end 28 forming a tapered, truncated conical shaped body portion on the proximal end of needle connector 20. Needle connector 20 has ribs 22 which engage lugs on the inside of a conventional protective sleeve (not shown) to permit rotation of needle connector 20 for removal of connector 20 from projection 19 on barrel 12. A needle 25 is carried by needle connector 20 and has a hollow passageway formed therein to permit flow of fluid into or out of bore 14.

Syringe 10 and needle connector 20 are of conventional design and form no part of the invention disclosed herein except in combination with the improved protective sleeve generally designated by the numeral 30, as will be hereinafter more fully explained.

Referring to FIG. 2 of the drawing, the protective needle guard sleeve 30 generally comprises a hollow cone shaped member 32 having a large end opening 34 and a small end opening 36 forming an interior guide surface 38.

A hollow tube 40 has an inner bore 42 into which spaced lugs 44 extend. The inner wall 41 of the tubular member is tapered. The inside diameter of passage 42 progressively decreases from opening 36 at the distal end of conical shaped cone 32 toward the closed distal end 45 of protective sleeve 30.

The inside diameter of opening 36 is greater than the outside diameter of portion 28 of needle connector 20 but less than the outside diameter of portion 26 of needle connector 20. Thus, when needle 25 and projections 22 on needle connector 20 are inserted into the bore 42 in protective sleeve 30 the outer surface of body portion 21 on connector 20 lying between portions 26 and 28 thereof will frictionally engage inner wall 41 of guard sleeve 30.

Lugs 44 are spaced from opening 36 to extend between and engage projections 22 on needle connector 20 to prevent rotation of guard sleeve 30 relative to needle connector 20.

A resilient collar 48 extends around the proximal end of hollow tubular sleeve 40 adjacent the reduced diameter end of hollow cone shaped member 32, forming a resilient deformable outer shoulder on the end of the hollow tube 40 to grippingly engage the central portion of tapered surface 21 on needle connector member 20 when it is urged into frictional engagement with the portion 43 of the inner surface 41 of tube 40.

From the foregoing it should be readily apparent that the structure hereinbefore described and illustrated in FIG. 2 of the drawing provides a protective needle guard 30 comprising a hollow cone 32 having a large end 34 and a small end 36 in combination with a hollow tube 40 secured to the small end of the hollow cone and that the hollow tube 40 has inner and outer walls 41 and 46, respectively. Shoulder 48 and internal surface 43 adjacent the distal end of tube 40 secure needle connector member 20 in needle guard 30 while the interengagement of lugs 44 and projections 22 permit removal of needle connector 20 from hypodermic syringe 10 to permit safe disposal of needle connector 20 and needle 25. In the embodiment of the needle guard sleeve 30 illustrated in FIGS. 1 and 2, shoulder 48 is in a plane which is spaced axially of tube 40 from the plane of lugs 44.

Hollow cone shaped member 32 having an enlarged proximal opening 34 is sufficiently large to shield the fingers of a health care worker against inadvertent needle stick injuries while needle 25 is being guided into passage 42 in the protective guard sleeve 30.

In the assembled condition, hollow connector sleeve 20 fits over and around tapered portion 19 of barrel 12 in tight fitting frictional engagement. Of course it will be appreciated that needle connector member 20 and barrel 12 may be secured together in numerous different fashions such as screw type threads. The distal end of cannula needle 25 forms a vein piercing sharp hollow point while the opposite end thereof functions as an orifice through which fluid may pass to or from passage 14 in barrel 12.

SECOND EMBODIMENT

The second embodiment of the invention illustrated in FIGS. 3 and 4 of the drawing comprises a blood collection system including a cannula tube 55, a cannula connector 60, an air evacuated collection container 70 and a protective sleeve 80.

Cannula tube 55 is of conventional design and is commercially available from Becton, Dickinson & Co. of Rutherford, N.J. under the registered trademark "VACUTAINER". Cannula tube 55 forms no part of the present invention except as a component used in combination with the novel design of connector 60 and protective sleeve 80 as will be hereinafter more fully explained. Cannula tube 55 comprises a hollow tube 56 having a hollow internally threaded shoulder 58 forming a connector portion into which externally threaded connector 60 is secured for mounting a double ended cannula.

Referring to FIG. 4 of the drawing, cannula connector 60 comprises a central body portion 62, an externally threaded proximal end portion 64 and a generally spline shaped distal end portion 66. A hollow needle extends through connector member 60 and has a distal end which forms a vein piercing sharp hollow needle 68 while the opposite end thereof functions as a cannula 69 positioned to pierce a resilient stopper in an air evacuated blood collection tube 70 as will be hereinafter more fully explained.

Cannula connector 60 is of conventional design except for the provision of the elongated central body portion 62 which spaces the splined portion 66 of connector member 60 from the end of threaded portion 64 a distance "D" as will be hereinafter more fully explained.

The air evacuated collection container 70 comprises a generally cylindrical body portion 72 having a closed distal end 73 and an open proximal end 74 forming an internal air evacuated chamber 75 inside body portion 72. A stopper 76 is formed of cannula pierceable material molded to form a generally cylindrical body portion having an enlarged head portion to form sealing surfaces engageable with surfaces on the proximal end of body 72.

The protective cover 80 illustrated in FIG. 3 of the drawing comprises a hollow tubular body 82 having a closed end 84 and an open end having a hollow bore 85 extending therethrough. A deformable elastomeric collar 86 extends around the exterior of body portion 82 and inwardly extending lugs 88 are formed inside bore 85. Collar 86 and lugs 88 lie in a common plane and are positioned such that when connector sleeve 60 is positioned in bore 85, lugs 88 engage the outer periphery of the splined portion 66 to grippingly engage splined portion 66 and central body portion 62 of connector 60. Collar 86 must be deformed or stretched for insertion of connector 60 into bore 85 such that protective sleeve 80 will be firmly secured to the end of cannula tube 55 to prevent removal thereof without application of substantial force to assure that the sleeve 80 will only be intentionally removed.

To protect the hand of a health worker inserting needle 68 into bore 85, an enlarged hollow funnelshaped head portion 90 is formed on the proximal end of sleeve 80 and forms a generally truncated conical shaped guide surface 95 converging toward the opening into bore 85 in sleeve 80. Head portion 90 and cannula connector 60 are preferably shaped and configured to permit use of sleeve 80 and cannula tube 55 in as near routine fashion as possible to assure that protective sleeve 80 is used without requiring any concentration or additional training of the health care worker.

The hollow needle 68 having a sharp pointed distal end secured by connector member 60 to the distal end of cannula tube 55 is enclosed in the hollow protective elastomeric sleeve 80. Bore 85 in sleeve 80 has an inside diameter which is less than the outside diameter of connector member 60. Shoulder 86 about the exterior of the open end of bore 85 in protective sleeve 80 forms a resilient deformable end section on the sleeve. The end section is deformable to grippingly engage the outside of the connector member. Guide member 90 has an enlarged proximal end and a reduced diameter distal end bounded by the inclined guide surface 95 configured to guide the sharp pointed hollow needle 68 into the open end of bore 85 in the elastomeric sleeve 80. Locking lugs 88 on the inner wall of bore 85 between opposite ends thereof detachably engage connector member 60 when the end of the connector member 60 is urged into deforming frictional engagement with the inner wall of sleeve 80 adjacent shoulder 86.

The elongated central body portion 62 of cannula connector 60 has a length which is equal to or greater than the depth "D" of the funnel shaped head 90 on protective sleeve 80 to cause the distal end of cannula tube 55 to be positioned adjacent the enlarged end 92 of funnel shaped head portion 90 of protective sleeve 80.

From the foregoing it should be readily apparent that the apparatus hereinbefore described incorporates safety features to protect a health care worker operating under emergency conditions to prevent accidental contact with potentially infectious blood samples without disrupting routine procedures of the worker.

Having described our invention, we claim:

1. A protective needle guard for a hypodermic syringe comprising: a hollow cone having a large end and a small end opening adjacent opposite ends of a uniformly converging guide surface; a hollow tube secured to the small end of said hollow cone, said tube having inner and outer walls and a central passage, said guide surface on said hollow cone being configured to guide a needle into said central passage in said hollow tube; a resilient deformable shoulder on said tube; and locking means on said inner wall adjacent an end of said tube to secure a needle in said tube, said cone being sufficiently large adjacent the large end to shield fingers of a health care worker against inadvertent needle stick injuries.

2. A protective needle guard according to claim 1, said shoulder being formed about the outer wall on the proximal end of said tube adjacent the small end of said hollow cone.

3. A protective needle guard according to claim 2 said locking mean son the inner wall of said tube comprising: circumferentially spaced lugs extending inwardly from said inner wall of said tube.

4. A protective needle guard according to claim 1, said locking means on the inner wall of said tube being adapted to prevent rotation of said hollow tube relative to a needle when the needle is positioned in said passage in said hollow tube.

5. A protective needle guard according to claim 1, said shoulder and said locking means lying in a common plane.

6. A protective needle guard according to claim 1, said shoulder and said locking means being spaced longitudinally of said tube.

7. A hypodermic syringe to inject liquid into a body or to withdraw body fluids comprising: a hollow container having a bore; closure means on the distal end of said container, said closure means having an opening formed therein; means associated with said container to change pressure in said bore to move fluid through said opening; a hollow needle having a sharp pointed distal end and a proximal end; a connector member for securing the proximal end of said hollow needle to the distal end of said container, said connector member having a non-circular distal end and a conical shaped proximal end; a hollow protective elastomeric sleeve having a closed end and an open end, said open end having an inside diameter which is less than the outside diameter of said connector member; a shoulder about the exterior of the open end of said protective sleeve forming a resilient deformable end section on said sleeve, said end section being deformable to grippingly engage the outer surface of said connector member; an enlarged hollow truncated conical shaped guide member secured to said shoulder, said guide member having an enlarged proximal end and a reduced diameter distal end bounded by an inclined guide surface configured to guide the sharp pointed hollow needle into the open end of said elastomeric sleeve; and locking means on the inner wall of said protective sleeve between opposite ends thereof to detachably engage said non-circular end of said connector member when said conical shaped end of said connector member is urged into deforming frictional engagement with the inner wall of said sleeve adjacent said shoulder.

8. A system for collecting a blood sample including a container having a closed distal end, an open proximal end, an internal air evacuated chamber, an cannula pierceable resilient seal means closing said open end;

and a cannula tube, the improvement comprising: a hollow needle having two sharp pointed ends; a cannula connector member for securing said hollow needle to the distal end of said cannula tube, said connector member having an elongated central body portion and a non-circular distal end; a hollow protective elastomeric sleeve having a closed end and an open end, said open end having an inside diameter which is less than the outside diameter of said cannula connector member; a shoulder about the exterior of the open end of said protective sleeve forming a resilient deformable end section on said sleeve, said end section being deformable to grippingly engage the outside of said connector member; and an enlarged hollow truncated conical shaped guide member secured to said shoulder, said guide member having an enlarged proximal end and a reduced diameter distal end bounded by an inclined guide surface configured to guide one of the sharp pointed hollow needles into the open end of said elastomeric sleeve; locking means on the inner wall of said protective sleeve between opposite ends thereof to detachable engage said non-circular end of said connector member when said connector member is urged into deforming frictional engagement with the inner wall of said sleeve adjacent said shoulder.

* * * * *

UNITED STATES PATENT AND TRADEMARK OFFICE
CERTIFICATE OF CORRECTION

PATENT NO. : 5,002,536

DATED : March 26, 1991

INVENTOR(S) : John P. Thompson and Ivy L. Thompson

It is certified that error appears in the above-identified patent and that said Letters Patent is hereby corrected as shown below:

Column 6, line 3, after "end" and before "and" insert

-- , said hollow cone having a large end opening --

Signed and Sealed this

Eighteenth Day of August, 1992

*Attest:*

DOUGLAS B. COMER

*Attesting Officer*     *Acting Commissioner of Patents and Trademarks*